United States Patent
Kouno et al.

(10) Patent No.: US 6,495,717 B1
(45) Date of Patent: Dec. 17, 2002

(54) PROCESS FOR PRODUCING SORBIC ACID OR SALTS THEREOF

(75) Inventors: Mitsuhiro Kouno, Arai (JP); Noboru Kamei, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/572,496

(22) Filed: May 18, 2000

(30) Foreign Application Priority Data

May 18, 1999 (JP) ............................................. 11-137750

(51) Int. Cl.$^7$ ............................................. C07C 57/10
(52) U.S. Cl. ....................................................... 562/601
(58) Field of Search ......................................... 562/601

(56) References Cited

U.S. PATENT DOCUMENTS 3,997,598 A * 12/1976 Fernholz et al.

FOREIGN PATENT DOCUMENTS

| DE | B1291738 | 4/1969 |
| EP | A10559239 | 8/1993 |
| GB | A1175006 | 12/1969 |
| JP | 4426646 | 11/1969 |
| JP | 54163516 A | 12/1979 |
| JP | 627097 B2 | 4/1994 |

OTHER PUBLICATIONS

CAPLUS abstract of JP 6107535 A2. Kamei et al. (1986). Sorbic Acid.*
Derwent abstract of CA 860971 A. Sorbic acid salts prodn under inert gas (1971).*
Derwent abstract of JP 62148448 A2. Kamei et al. (1987). Storage of wet sorbic acid cake—without deterioration and colouring by shielding with inert gas.*

* cited by examiner

Primary Examiner—Paul J. Killos
(74) Attorney, Agent, or Firm—Birch, Stewart, Kolasch & Birch, LLP

(57) ABSTRACT

A process produces sorbic acid or its salt and includes the step of retaining a slurry or solution containing sorbic acid or its salt while holding an oxygen concentration of a gaseous phase at 4% by volume or less, the gaseous phase being in contact with the slurry or solution containing sorbic acid or its salt. In the process, the oxygen concentration of the gaseous phase may be held at 4% by volume or less while introducing an inert gas into a gaseous phase of a reservoir holding the slurry or solution and/or of a conduit adjacent to the reservoir. Such an inert gases includes, for example, nitrogen gas. The oxygen concentration of the gaseous phase is preferably held at 1% by volume or less. The process can prevent the formation of new color-inducing substances in a purification operation of sorbic acid or its salt, and the obtained sorbic acid or its salt has a minimized degree of coloring and a minimized deterioration of hue over time.

4 Claims, No Drawings

PROCESS FOR PRODUCING SORBIC ACID OR SALTS THEREOF

BACKGROUND OF THE INVENTION

1. Field of the Invention

This invention relates to a process for producing sorbic acid or its salt which is useful as, for example, a food additive. Particularly, the invention relates to a process for producing sorbic acid or its salt that has a minimized coloring and a minimized deterioration of hue over time.

2. Description of the Related Art

In various known processes for producing sorbic acid or its salt, a commercially important pathway is a process of polymerizing crotonaldehyde and ketene to form an intermediate polyester, and decomposing the polyester to yield sorbic acid. The polyester is decomposed, for example, by the aid of hydrochloric acid, an alkali or heat to yield a crude sorbic acid. The thus-prepared crude sorbic acid generally contains a variety of colored substances, tar substances, and other impurities with varying degrees of concentration, and is subjected to a purification operation.

As purification processes of sorbic acid or its salt, a treatment with activated carbon, recrystallization with water or with a mixture of water and an organic solvent, and distillation purification of a solution of sorbic acid or its salt in petroleum have been known. For example, Japanese Unexamined Patent Application Publication No. 54-163516 discloses a purification process. This process includes the steps of preparing a polyester from ketene and crotonaldehyde, decomposing the polyester with hydrochloric acid in the presence of, for example, a urea compound to yield a decomposition reaction mixture, separating the decomposition reaction mixture by filtration, and washing the residue to yield a crude sorbic acid, adding a sodium hydroxide aqueous solution to the crude sorbic acid to yield a sodium sorbate aqueous solution, treating the aqueous solution with activated carbon, neutralizing the treated solution, and cooling the neutralized solution to crystallize sorbic acid.

Japanese Examined Patent Application Publication No. 44-26646 discloses a process for producing a crystalline sorbic acid. The process includes the steps of preparing a polyester from ketene and crotonaldehyde, decomposing the polyester with hydrochloric acid having a concentration of 35% by weight or more at temperatures ranging from room temperature to around the boiling point of the hydrochloric acid used, cooling the reaction mixture, separating a crude sorbic acid by filtration, washing the crude sorbic acid with water, putting the washed crude sorbic acid into water, heating and dissolving the mixture to yield a solution, adding activated carbon to the solution, boiling the mixture, and filtering the mixture while heating, and gradually cooling the resulting filtrate to yield a crystalline sorbic acid.

Japanese Examined Patent Application Publication No. 6-27097 discloses a process for preventing the deterioration of sorbic acid. The process includes the steps of retaining a sorbic acid wet cake in an inert gas and holding the oxygen concentration in a system at 10 parts by volume or less. The sorbic acid wet cake is formed in a production process of sorbic acid and contains water and/or a solvent.

A problem of sorbic acid or an alkali sorbate purified according to the above techniques is a tendency to color after drying, which is induced by the formation of new impurities, to thereby deteriorate the commercial value of a resulting product, although no deterioration of appearance as a solid mater or an aqueous solution is observed before drying. In this connection, even if a wet cake of sorbic acid is stored in an inert gas as in the above publication, the degree of coloring of sorbic acid increases with the passage of time after drying, when a color-inducing substance is formed before the storage. Desired advantages according to this technique cannot be significantly obtained.

SUMMARY OF THE INVENTION

Accordingly, an object of the invention is to provide a process for producing sorbic acid or its salt, which can prevent the formation of a new color-inducing substance in a purification operation of sorbic acid or its salt, where the obtained sorbic acid or its salt has a minimized degree of coloring and a minimized deterioration of hue over time.

The present inventors made intensive investigations to achieve the above object, and found that when a slurry or solution of sorbic acid or its salt in production operations of sorbic acid or its salt is left standing, the hue of a sorbic acid or its salt obtained by separating the slurry or solution is deteriorated with time, and that this deterioration of hue with time can be prevented by holding the slurry or solution of sorbic acid or its salt in an atmosphere at an oxygen concentration under a specific level. The present invention has been accomplished based on these findings.

Specifically, the invention provides a process for producing sorbic acid or its salt. The process includes the step of retaining a slurry or solution containing sorbic acid or its salt while holding an oxygen concentration of a gaseous phase at 4% by volume or less, which gaseous phase is in contact with the slurry or solution containing sorbic acid or its salt.

In the above production process, the oxygen concentration of the gaseous phase may be held at 4% by volume or less while introducing an inert gas into a gaseous phase of a reservoir holding the slurry or solution containing sorbic acid or its salt, or of a conduit adjacent to the reservoir, or of both. Such inert gases include, but are not limited to, a nitrogen gas. The oxygen concentration of the gaseous phase is preferably held at 1% by volume or less.

DESCRIPTION OF THE PREFERRED EMBODIMENT

Slurries or solutions containing sorbic acid or its salt for use in the invented process are not critical and include slurries or solutions obtained by any process. Such slurries or solutions include, but are not limited to, slurries or solutions (particularly aqueous slurries or solutions) at each step in a purification operation of sorbic acid formed by the decomposition of a polyester, which polyester is obtained from ketene and crotonaldehyde, or in a purification operation of an alkali sorbate obtained by allowing an alkali to act upon the sorbic acid.

The reaction of ketene with crotonaldehyde is generally performed in the presence of a catalyst and in the absence of or in the presence of an inert solvent. Such catalysts include, for example, simple substances or compounds of manganese, cobalt, nickel, zinc, cadmium, and other transition metals; and pyridine, picoline, and other nitrogen-containing basic compounds. Examples of the compounds of the transition metals are oxides; salts of acetic acid, salts of isobutyric acid, salts of isovaleric acid, and salts of other organic acids; salts of sulfuric acid, salts of nitric acid, and salts of other inorganic acids; chlorides and other halides; acetylacetone complex salt, and other complex salts and complexes. Each of these catalysts can be used alone or in combination. The amount of the catalyst differs according to the type of the catalyst, but is generally about 0.1 to 10% by weight relative to the weight of ketene. The reaction of ketene with crotonaldehyde is performed at a temperature of, for example, about 2° C. to 100° C.

A reaction mixture containing a polyester obtained through the reaction of ketene with crotonaldehyde is usually distilled to remove unreacted crotonaldehyde and low boiling impurities, and is then subjected to a decomposition reaction. The polyester may be decomposed by any of hydrolysis with an acid or alkali or thermal decomposition, but should be preferably decomposed by hydrolysis with a mineral acid, especially with hydrochloric acid, for a high yield. The polyester is hydrolyzed at a reaction temperature of, for example, about 10° C. to 110° C. An extremely low reaction temperature will result in a deteriorated reaction efficiency, and in contrast, an extremely high reaction temperature may increase amounts of by-produced impurities such as tar substances. When the polyester is hydrolyzed with hydrochloric acid, the concentration of hydrochloric acid is, for example, about 15 to 40% by weight. An extremely low concentration of hydrochloric acid may invite a decreased reaction rate, and in contrast, an extremely high concentration of hydrochloric acid may invite disadvantages in handling property or operability. The amount of hydrochloric acid ranges, as hydrogen chloride, for example, from about 10 to 160 parts by weight relative to 100 parts by weight of the polyester.

A reaction mixture obtained through the decomposition of the polyester contains sorbic acid or its salt, a catalyst used in the reaction, as well as colored substances, tar substances, and other impurities by-produced in the reaction. Accordingly, the production of sorbic acid or its salt of high quality requires a purification operation. Such purification processes of a crude sorbic acid include, for example, (i) a process of preparing an aqueous solution of an alkali sorbate using a crude sorbic acid, treating the aqueous solution with activated carbon, acidifying the treated solution to yield a slurry of sorbic acid, and separating sorbic acid by filtration, (ii) a process of dissolving a crude sorbic acid in a hot water, treating the resulting solution with activated carbon, cooling the treated solution to yield a slurry of sorbic acid, and separating the slurry by filtration, (iii) a process of crystallizing sorbic acid with water or a mixture of water and an organic solvent (e.g., methanol, ethanol, or isopropyl alcohol) or further subjecting the crystallized sorbic acid to recrystallization, (iv) a process of dissolving a crude sorbic acid in petroleum, and distilling the resulting solution, and combinations of these processes. A purification process of a salt of sorbic acid includes, for example, a treatment with activated carbon.

The present invention has a feature in that an oxygen concentration of a gaseous phase in contact with a slurry or solution containing sorbic acid or its salt is held at 4% by volume or less where the slurry or solution is retained as intact for a predetermined period in such a production process of sorbic acid or its salt as mentioned above.

The present inventors found that when sorbic acid or its salt is present as a slurry or a solution in a production process thereof, the sorbic acid or its salt markedly deteriorates at a lower concentration of oxygen than sorbic acid or its salt as a wet cake. This is speculated to be induced by the following mechanism. In a slurry or solution containing sorbic acid or its salt prior to the completion of purification, impurities as precursors of colored substances are predominantly present in an aqueous phase, and the impurities are reacted with oxygen to readily deteriorate. These deteriorated impurities cannot be readily removed by rinsing crystals obtained by, for example, draining of a slurry, provably because of a high affinity of the impurities to sorbic acid or its salt, and are attached to and accompanied with crystals of sorbic acid or its salt to a drying operation and are converted into colored substances on exposure to heat. When an alkali salt of sorbic aid is prepared by neutralizing sorbic acid containing the deteriorated impurities with an alkali, the hue of an aqueous solution of the alkali sorbate after neutralization is deteriorated, and the color valency of an alkali sorbate obtained by concentrating and drying the aqueous solution is markedly deteriorated. In addition, when the alkali sorbate is stored in the air, the hue is further deteriorated with time.

However, according to the present invention, the oxygen of a gaseous phase is controlled to a markedly low concentration where sorbic acid or its salt is in a slurry or in a solution, and the resulting purified sorbic acid or its salt shows a markedly minimized deterioration of hue even in a long-term storage as a dried product in the air. This is provably because the deterioration of impurities in an aqueous phase is markedly suppressed and the impurities can be easily removed by, for example, rinsing with water and are not accompanied with crystallized sorbic acid or its salt. For example, if a sorbic acid slurry stored according to the invented process is filtered to yield a wet cake of sorbic acid, and the wet cake is neutralized to yield an alkali sorbate, the hue of the resulting product is of equal quality to an alkali sorbate obtained by filtering the sorbic acid slurry immediately after preparation to yield a sorbic acid wet cake and neutralizing the wet cake. Such hue of products includes the hue of the alkali sorbate aqueous solution, the hue of an alkali sorbate obtained by concentrating and drying the alkali sorbate aqueous solution, and the hue of the alkali sorbate after a long-term storage in the air.

According to the invented process, it is not necessary to feed a slurry or solution containing sorbic acid or its salt to a subsequent operation immediately after preparation, and a required portion of the slurry or solution can be fed to the subsequent operation at desired point of time. Such subsequent operations include, for example, a filtration operation, a treating operation with activated carbon, and an acidifying operation. A plan for the production of sorbic acid or its salt can be easily set up to provide an improved production efficiency.

The oxygen concentration of a gaseous phase in contact with the slurry or solution containing sorbic acid or its salt may be held at 4% by volume or less by simple replacement of the air in a gaseous phase of a reservoir containing the slurry or solution or of a conduit adjacent to the reservoir by an inert gas. Especially in the use of a slurry, the slurry is usually homogenized by agitation to facilitate supply of the slurry, and a contact surface with the air is continuously renewed and a gaseous phase is readily caught in a liquid phase. The oxygen concentration is therefore effectively held under a specific level while continuously or intermittently introducing an inert gas to the gaseous phase of the reservoir and/or the conduit.

The gaseous phase of the slurry or solution of sorbic acid or its salt has an oxygen concentration of preferably 1% by volume or less, more preferably 0.5% by volume or less, and particularly preferably 0% by volume. In this case, the slurry or solution is completely sealed with an inert gas. Generally, the product sorbic acid or its salt is more deteriorated with an increasing temperature. However, if the slurry or solution is completely sealed with an inert gas, the product sorbic acid or its salt has a significantly stable color value even if the slurry or solution rises in temperature to about 50° C.

Inert gases for use in the invention include, for example, nitrogen gas, carbon dioxide gas, and argon gas, and nitrogen gas is commercially advantageously used.

As described above, a slurry of sorbic acid stored according to the invented process can yield a wet cake of sorbic acid having a higher quality by draining the slurry. Impurities which are not deteriorated and are holding water-solubility can be easily removed by rinsing the wet cake with water. In the draining and rinsing procedures, the oxygen concentration in a system should be preferably minimized with an inert gas, especially to 0%. Sorbic acid can be obtained by drying the wet cake of sorbic acid, or crystallizing or recrystallizing the same according to necessity.

Alkalis for use in the neutralization of the wet cake to yield an alkali sorbate include, for example, hydroxides, carbonates, and bicarbonates of sodium, potassium, and other alkali metals. Of these alkalis, potassium hydroxide or potassium salts should be advantageously employed for obtaining an alkali sorbate with a less deterioration over time. An alkali sorbate aqueous solution after the completion of neutralization is concentrated, is dried, and is granulated according to a conventional known technique.

The product sorbic acid or its salt can be used as preservatives for foods such as fish pastes, butters, cheeses, bean pastes, and jams.

The invented process, where the oxygen concentration of a gaseous phase is held under a specific level, can prevent the formation of new color-inducing substances in a purification operation of sorbic acid or its salt and can easily produce a high quality sorbic acid or its salt having a highly stable hue over time.

The present invention will now be illustrated in further detail with reference to several inventive examples, comparative examples, and reference examples below, which are not intended limiting the scope of the invention.

REFERENCE EXAMPLE 1

A crude sorbic acid was prepared by decomposing a polyester with hydrochloric acid, which polyester was obtained by a reaction of ketene with crotonaldehyde. A total of 100 g of the crude sorbic acid (moisture content: 20% by weight, tar content: 4% by weight, sorbic acid: 76% by weight) was dissolved in a 5% by weight sodium hydroxide aqueous solution. To the resulting solution, 0.5 g of activated carbon was added and the mixture was stirred for 30 minutes. The treated mixture was then filtered to yield a filtrate, and an excess volume of a 35% by weight hydrochloric acid was added to the filtrate to precipitate sorbic acid, and the precipitated sorbic acid was fractionated by filtration. The obtained sorbic acid wet cake was recrystallized with a water-ethanol mixture solvent to yield a sorbic acid slurry, and the slurry was immediately fractionated by filtration to yield 90 g of a purified sorbic acid wet cake (moisture content: 10% by weight, ethanol: 10% by weight, sorbic acid: 80% by weight) A total of 33 g of water was added to 50 g of the purified sorbic acid wet cake, and the mixture was neutralized with a 49% by weight potassium hydroxide (KOH) aqueous solution.

The above-prepared potassium sorbate aqueous solution was found to have a color valency of 98.0% as determined as a light transmittance at a wavelength of 430 nm with a spectrophotometer. The aqueous solution was dried under reduced pressure (30 mmHg, 55° C.) to yield 88 g of potassium sorbate. The potassium sorbate had a color valency of 98.0% as determined by dissolving 2 g of the potassium sorbate in water to make 10 ml, and determining the light transmittance of the aqueous solution at 430 nm with a spectrophotometer. The potassium sorbate was air-sealed and was left for 6 months, and was then found to have a color valency of 94.5%.

EXAMPLE 1

The procedure of Reference Example 1 was repeated, except that a purified sorbic acid wet cake was obtained by preparing a sorbic acid slurry through recrystallization with a water-ethanol solvent, stirring the slurry for 5 hours while sealing the slurry with a pure nitrogen at an oxygen concentration of about 0% by volume, and fractionating the slurry by filtration. A potassium sorbate aqueous solution after neutralization had a color valency of 98.0%, and potassium sorbate obtained by drying the aqueous solution had a color valency of 97.8%. These color valencies were of equal quality to those obtained in Reference Example 1, where the sorbic acid slurry was immediately fractionated by filtration without standing. The potassium sorbate was air-sealed and was left for 6 months, and was then found to have a color valency of 94.5%.

COMPARATIVE EXAMPLE 1

The procedure of Example 1 was repeated, except that a purified sorbic acid wet cake was obtained by preparing a sorbic acid slurry through recrystallization with a water-ethanol mixture solvent, stirring the slurry for 5 hours while sealing the slurry with nitrogen at an oxygen concentration of a gaseous phase of 5% by volume, and fractionating the slurry by filtration. A potassium sorbate aqueous solution after neutralization had a decreased color valency of 97.2%, and potassium sorbate obtained by drying the aqueous solution had a decreased color valency of 96.2%. The potassium sorbate was air-sealed and was left for 6 months, and was then found to have a color valency of 91.2%.

COMPARATIVE EXAMPLE 2

The procedure of Comparative Example 1 was repeated, except that the stirring time was changed to 1 hour. As a result, a potassium sorbate aqueous solution after neutralization had a color valency of 97.4%, and potassium sorbate obtained by drying the aqueous solution had a color valency of 96.5%. The potassium sorbate was air-sealed and was left for 6 months, and was then found to have a color valency of 91.8%.

REFERENCE EXAMPLE 2

A crude sorbic acid was prepared by decomposing a polyester with hydrochloric acid, which polyester was prepared by a reaction of ketene with crotonaldehyde. A total of 100 g of the crude sorbic acid (moisture content: 20% by weight, tar content: 4% by weight, sorbic acid: 76% by weight) was dissolved at 120° C. in 320 g of a commercially available lubricating oil having a boiling point ranging from 200° C. to 250° C. The solution was heated and evaporated at a pressure of 30 mmHg till a bottom temperature reached 170° C. The vapor was purified with a packed mist separator, was then cooled and condensed with a contact condenser in which water was circulated and was collected as a slurry mixture of water, lubricating oil, and sorbic acid. The slurry mixture was immediately filtered to yield 102 g of a purified sorbic acid wet cake (moisture content: 20% by weight, ethanol: 10% by weight, sorbic acid: 70% by weight). A total of 33 g of water was added to 50 g of the purified sorbic acid wet cake, and the mixture was neutralized with a 49% by weight potassium hydroxide (KOH) aqueous solution. The neutralized solution was allowed to stand to separate and remove the lubricating oil content. To the resulting solution, 1 g of activated carbon (SHIRASAGI A, a product of Takeda Chemical Industries, Ltd.) was added and the mixture was stirred for 30 minutes. The treated mixture was filtered, and the color valency of the filtrate was determined as a light transmittance at a wavelength of 430 nm with a spectrophotometer and was found to be 98.0%. The aqueous solution was dried under reduced pressure (30 mmHg, 55° C.) to yield 46 g of potassium sorbate. The potassium sorbate had a color valency of 98.0% as determined by dissolving 2 g of the potassium sorbate in water to make 10 ml, and determining the light transmittance of the aqueous solution at 430 nm with a spectrophotometer. The potassium sorbate was air-sealed and was left for 6 months, and was then found to have a color valency of 94.5%.

EXAMPLE 2

The procedure of Reference Example 2 was repeated, except that a purified sorbic acid wet cake was prepared by stirring the slurry mixture containing water, lubricating oil and sorbic acid for 5 hours while sealing the slurry with a pure nitrogen at an oxygen concentration of a gaseous phase of about 0% by volume, and fractionating the slurry by filtration. A potassium sorbate aqueous solution after neutralization and treatment with activated carbon had a color valency of 98.0%, and potassium sorbate obtained by drying the aqueous solution had a color valency of 97.7%. These color valencies were of equal quality to those obtained in Reference Example 2, where the slurry was immediately fractionated by filtration without standing. The potassium sorbate was air-sealed and was left for 6 months, and was then found to have a color valency of 94.2%.

EXAMPLE 3

The procedure of Example 2 was repeated, except that the slurry mixture was heated and was stirred at 50° C. A potassium sorbate aqueous solution after neutralization and treatment with activated carbon had a color valency of 97.8%, and potassium sorbate obtained by drying the aqueous solution had a color valency of 97.4%. These color valencies were of equal quality to those obtained in Reference Example 2, where the slurry was immediately fractionated by filtration without standing. The potassium sorbate was air-sealed and was left for 6 months, and was then found to have a color valency of 94.0%.

COMPARATIVE EXAMPLE 3

The procedure of Example 2 was repeated, except that the slurry mixture containing water, lubricating oil and sorbic acid was sealed by introducing nitrogen to provide the oxygen concentration of a gaseous phase of 5% and the sealed slurry was stirred for 5 hours. A potassium sorbate aqueous solution after neutralization and treatment with activated carbon had a decreased color valency of 97.1%, and potassium sorbate obtained by drying the aqueous solution had a decreased color valency of 94.8%. The potassium sorbate was air-sealed and was left for 6 months, and was then found to have a color valency of 90.9%.

COMPARATIVE EXAMPLE 4

The procedure of Comparative Example 3 was repeated, except that the stirring time was changed to 1 hour. As a result, a potassium sorbate aqueous solution after neutralization and treatment with activated carbon had a color valency of 97.4%, and potassium sorbate obtained by drying the aqueous solution had a color valency of 95.3%. The potassium sorbate was air-sealed and was left for 6 months, and was then found to have a color valency of 91.5%.

COMPARATIVE EXAMPLE 5

The procedure of Example 2 was repeated, except that the slurry mixture was stirred for 5 hours without sealing with nitrogen gas. That is, the gaseous phase above the slurry was air during the stirring. A potassium sorbate aqueous solution after neutralization and treatment with activated carbon had a decreased color valency of 96.2%, and potassium sorbate obtained by drying the aqueous solution had a decreased color valency of 88.3%. The potassium sorbate was air-sealed and was left for 6 months, and was then found to have a color valency of 81.3%.

Other embodiments and variations will be obvious to those skilled in the art, and this invention is not to be limited to the specific matters stated above.

What is claimed is:

1. A process for decreasing the level of discoloration and deterioration of hue for at least six months in sorbic acid or its salt, said process comprising the steps of retaining a slurry containing sorbic acid or its salt for 1 hour or more while holding an oxygen concentration of a gaseous phase at 1% by volume or less, said gaseous phase being in contact with said slurry containing sorbic acid or its salt, draining the slurry to yield a wet cake of sorbic acid or its salt, rinsing the wet cake with water, and air sealing a solid of sorbic acid or its salt obtained from the wet cake of sorbic acid or its salt.

2. The process of claim 1, wherein the oxygen concentration of said gaseous phase is held at 1% by volume or less while introducing an inert gas into a gaseous phase of a reservoir holding said slurry containing sorbic acid or its salt, or of a conduit adjacent to said reservoir, or of both.

3. The process of claim 2, wherein said inert gas is a nitrogen gas.

4. The process of claim 1, wherein the oxygen concentration of the gaseous phase is held at about 0% by volume.

* * * * *